United States Patent
Liang et al.

(10) Patent No.: US 10,295,164 B2
(45) Date of Patent: May 21, 2019

(54) ILLUMINATION CONTROL DEVICE OF SURGICAL LIGHT

(71) Applicant: Amtai Medical Equipment, Inc., Raleigh, NC (US)

(72) Inventors: Clay Liang, Raleigh, NC (US); Wei-Li Wu, Taichung (TW); Chih-Cheng Tseng, Taoyuan (TW)

(73) Assignee: AMTAI MEDICAL EQUIPMENT, INC., Raleigh, NC (US)

( * ) Notice: Subject to any disclaimer, the term of this patent is extended or adjusted under 35 U.S.C. 154(b) by 0 days.

(21) Appl. No.: 15/957,911

(22) Filed: Apr. 20, 2018

(65) Prior Publication Data

US 2018/0238529 A1 Aug. 23, 2018

Related U.S. Application Data

(63) Continuation-in-part of application No. 15/058,159, filed on Mar. 2, 2016, now abandoned.

(51) Int. Cl.
*F21V 23/04* (2006.01)
*F21V 21/40* (2006.01)
(Continued)

(52) U.S. Cl.
CPC .......... *F21V 23/0435* (2013.01); *A61B 90/35* (2016.02); *F21V 21/40* (2013.01); *F21V 23/003* (2013.01); *F21V 23/045* (2013.01); *H05B 37/02* (2013.01); *H05B 37/0227* (2013.01); *A61B 2090/308* (2016.02); *F21S 8/043* (2013.01); *F21S 8/063* (2013.01); *F21V 21/28* (2013.01); *F21W 2131/205* (2013.01)

(58) Field of Classification Search
CPC .. F21V 23/0435; F21V 23/045; F21V 23/003; F21V 21/403; A61B 90/30; A61B 90/308; A61B 90/35; F21W 2131/205
USPC ........................................ 362/804; 602/2–19
See application file for complete search history.

(56) References Cited

U.S. PATENT DOCUMENTS 5,014,080 A * 5/1991 Miyadera ................. G02B 7/32
 396/106
5,526,245 A * 6/1996 Davis ...................... F21S 8/026
 362/233

(Continued)

*Primary Examiner* — Anh T Mai
*Assistant Examiner* — Michael Chiang
(74) *Attorney, Agent, or Firm* — Leong C. Lei

(57) ABSTRACT

A surgical lighting illumination control device includes a suspension system; light heads mounted on the suspension system and each including a housing, light sources mounted in the housing, an unsterilizable grip mounted on the housing for hand holding and moving the light heads, and detection pairs mounted to the unsterilizable grip for receiving an infrared signal that is transmitted therefrom and reflected by an external object for control and adjustment of the illumination, each detection pair including an infrared transmitter and an infrared receiver; a compensation control mechanism connected to the detection pairs and including a control operation unit and environment temperature compensation units connected to the control operation unit; and a sterilizable grip mountable to the unsterilizable grip and including a guide channel formed therein to correspond, in position, to each of the detection pairs to allow the infrared signal to pass therethrough.

14 Claims, 5 Drawing Sheets

(51) Int. Cl.
*F21V 23/00* (2015.01)
*A61B 90/35* (2016.01)
*H05B 37/02* (2006.01)
*F21V 21/28* (2006.01)
*A61B 90/30* (2016.01)
*F21W 131/205* (2006.01)
*F21S 8/04* (2006.01)
*F21S 8/06* (2006.01)

(56) References Cited

U.S. PATENT DOCUMENTS

| | | | | |
|---|---|---|---|---|
| 5,637,863 | A * | 6/1997 | Sanborn | F21V 23/04 250/221 |
| 6,069,457 | A * | 5/2000 | Bogdan | H02J 13/0048 315/265 |
| 6,692,141 | B2 * | 2/2004 | Jesurun | F21V 21/403 362/399 |
| 7,321,385 | B2 * | 1/2008 | Rus | H04N 5/23216 348/135 |
| 2010/0026994 | A1 * | 2/2010 | Bove | G01D 5/26 356/138 |
| 2018/0209623 | A1 * | 7/2018 | Strolin | F21V 21/403 |

* cited by examiner

ILLUMINATION CONTROL DEVICE OF SURGICAL LIGHT

CROSS-REFERENCE TO RELATED APPLICATION

This is a continuation-in-part of co-pending U.S. patent application Ser. No. 15/058,159 filed on Mar. 2, 2016.

(a) TECHNICAL FIELD OF THE INVENTION

The present invention relates generally to innovation associated with an illumination control device of surgical light, and more particularly to one allowing surgeons to control, during the process of a surgical operation, the illumination by themselves to instruct medical personnel to control the illumination from a location outside a sterile area by means of an infrared remote controller so as to improve the efficiency of surgical operations and reduce patients' risk of infection and also reduce the expenditure of manufacture.

(b) DESCRIPTION OF THE PRIOR ART

US Patent Application Publication No. 2007/0030702 describes techniques that a control interface for operating an illumination function of a surgical light is mounted to a suspension arm thereof at a location close to a light head, or is mounted to the light heads at a location that is close to the suspension arm. Such a device requires no installation of a control interface on a wall so that engineering cost of installation and wire laying can be eliminated. However, the following three drawbacks exist:

Firstly, the control interface is mounted in a sterile area of a surgical room. If a surgeon is allowed to operate it during the process of a surgical operation, there might potential risk of infection of the patient. Thus, the surgeons must instruct other medical personnel located outside the sterile area to operate the control interface in order to control the illumination. Thus, the surgeons must wait for the operation of the control interface by the medical personnel to be completed before the lighting necessary for illumination can be obtained. This makes it necessary to have other medical personnel stand by during the process of the surgical operation, leading to the time required for operating the control interface extended for achieving proper adjustment and control of the lighting, and additional human labor of medical personnel must be involved.

Secondly, the control interface is generally mounted at a location very close to an operation area of a surgical room. If medical personnel who are in a condition of proper disinfection are allowed to operate the control interface, then contaminant, bacteria, or virus carried on their suits may entrain air streams that flow downward from the ceiling of the surgical room to get into the incision openings of the patient, leading to an increase of the potential risk of infection.

Thirdly, some surgical operations may be conducted collaboratively by multiple surgeons and the sterile areas around the surgical table would be full of medical personnel including surgeons, anesthetists, and nurses, making it not possible for other medical personnel to get approaching the light heads of the surgical light that are generally located above the surgical table for operating the control interface. This makes it necessary to install a wall-mounted control interface for the surgical room to allow for access and operation of the control interface from outside the sterile area by the other medical personnel. This makes it not possible to save the cost of installation and wire laying of the wall-mounted control interface.

To overcome such drawbacks and shortcomings, techniques, such as the disclosure of US Patent Application Publication No. 2003/0210559, have been proposed, where pushbuttons for operating a light head of a surgical light are provided on an outer circumference of a trapezoidal cylindrical projection formed under the light head of the surgical light, for ready access by a surgeon during a surgical operation to control the light head of the surgical light by himself or herself and also for adjusting the parameters of illumination without increasing the patients' risk of infection. Further, when the surgeons are not able to operate the push button by themselves, other medical personnel is allowed to operate a wall-mounted control interface for adjusting the illumination parameters. This technique, allowing eliminating the above-discussed drawbacks, still suffers the following problems:

Since the cylindrical projection formed under the light head of the surgical light and the pushbutton mounted thereon are located in an unsterilizable area, surgeons and/or medical personnel are not allowed to directly contact it. Thus, a transparent flexible cover that is properly sterilized must be provided and mounted to the cylindrical projection to allow for contact and touch by surgeons and medical personnel to operate the pushbuttons. However, such a transparent flexible cover is a disposable consumable material and must be disposed of after use. This increases the expenditure of the consumable material for surgical operations. Further, additional cost of installation and wire laying for a wall-mounted control interface is also required.

SUMMARY OF THE INVENTION

The primary object of the present invention is to allow surgeons, when holding a sterilizable grip mounted to an unsterilizable grip during surgical procedures, to use hands to block a guide channel to have a signal from an infrared transmitter of a detection pair reflected back to an infrared receiver associated therewith in order to control illumination, or alternatively, to allow the surgeons, who are busy in carrying out a surgical operation and are not able to control illumination by themselves, to instruct medical personnel to control, from a location outside a sterile area, the illumination with an infrared remote controller, wherein a compensation control mechanism is provided for temperature compensation in operation thereof and for management of operation frequencies of the detection pairs. As such, the efficiency of surgical operations can be improved and advantages of reducing patients' risk of infection and expenditure can be achieved.

To achieve the above object, the present invention provides a surgical lighting illumination control device, which comprises: a suspension or support system; one or multiple light heads carried on the suspension or support system, each of the light heads comprising a housing, one or multiple light sources mounted in the housing for illumination, an unsterilizable grip mounted on the housing for hand holding and moving the light heads, and one or multiple detection pairs mounted to the unsterilizable grip and comprising an infrared transmitter and an infrared receiver for receiving an infrared signal that is transmitted therefrom and reflected by an external object for conducting control and adjustment of the illumination, each of the detection pairs comprising an infrared transmitter and an infrared receiver; a compensation control mechanism connected to each of the detection pairs and comprising a control operation unit and a plurality of environment temperature compensation units connected to the control operation unit; and a sterilizable grip mountable to the unsterilizable grip and comprising a guide channel formed therein to correspond, in position, to each of the detection pairs to allow the infrared signal to pass therethrough, allowing a surgeon to control the illumination while relocating the light heads and to block the guide channel with hands to have a signal transmitted from the infrared transmitter of the detection pair reflected back to the infrared receiver associated therewith. Or alternatively, the infrared receiver of the detection pair may receive an illumination control signal emitting from an external infrared remote controller.

In an embodiment of the present invention, the control operation unit comprises one of an integrated circuit.

In an embodiment of the present invention, each of the environment temperature compensation units comprises an amplifier connected to the control operation unit and a negative temperature coefficient (NTC) resistor connected to the amplifier.

In an embodiment of the present invention, the environment temperature compensation units are respectively connected to the infrared transmitters of the detection pairs.

In an embodiment of the present invention, the environment temperature compensation units are respectively connected to the infrared receivers of the detection pairs.

In an embodiment of the present invention, the surgical lighting illumination control device further comprises a plurality of current-limiting units connected to the control operation unit, the current-limiting units being respectively connected to the infrared transmitters of the detection pairs.

In an embodiment of the present invention, each of the current-limiting units comprises a current-limiting resistor.

In an embodiment of the present invention, the unsterilizable grip comprises three bidirectional illumination adjustment units mounted thereto, wherein each of the bidirectional illumination adjustment units comprises first and second detection pairs for controlling multiple light functions.

In an embodiment of the present invention, the activation and illumination intensity of the light sources is controlled by a light source driver coupled to each of the detection pairs.

In an embodiment of the present invention, when the infrared receiver of the first detection pair receives a signal transmitted from the infrared transmitter of the first detection pair, the light source driver is operable to sequentially increment illumination intensity of the light sources; and when the infrared receiver of the second detection pair receives a signal transmitted from the infrared transmitter of the second detection pair, the light source driver is operable to sequentially decrement illumination intensity of the light sources.

In an embodiment of the present invention, when the infrared receivers of the first detection pair and the second detection pair simultaneously receive signals transmitted from the infrared transmitters respectively associated therewith, the light source driver activates or deactivates the light sources.

In an embodiment of the present invention, the infrared receiver of each of the detection pairs is operable in combination with a signal of an external infrared remote controller so that the infrared receiver of the detection pair may receive an illumination control signal emitting from the infrared remote controller.

In an embodiment of the present invention, the sterilizable grip is structured for mounting/dismounting without use of a tool and is repeatedly sterilizable for repeated use.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

Figure 1:
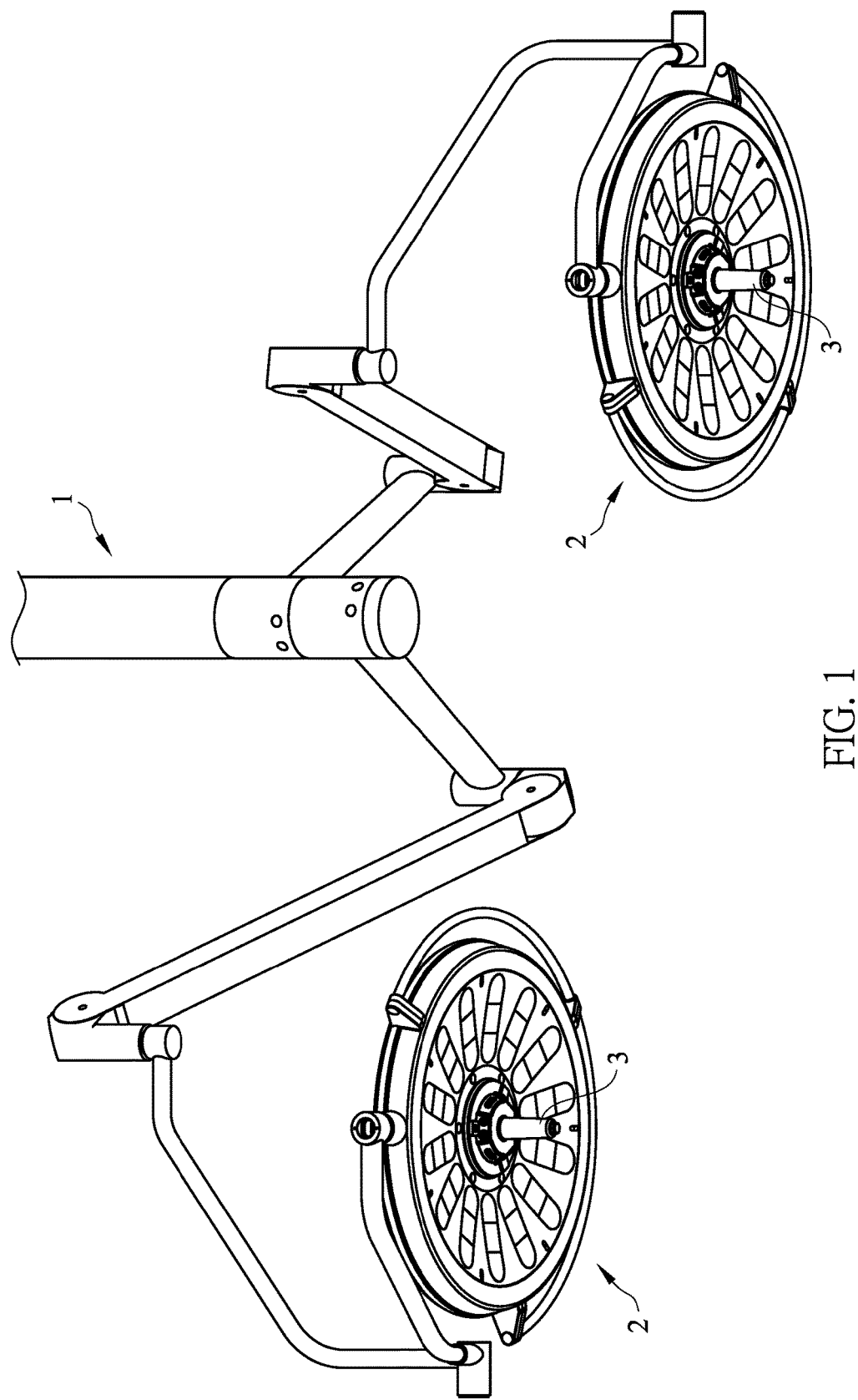
FIG. 1 is a schematic view illustrating an entire arrangement of the present invention.
Figure 2:
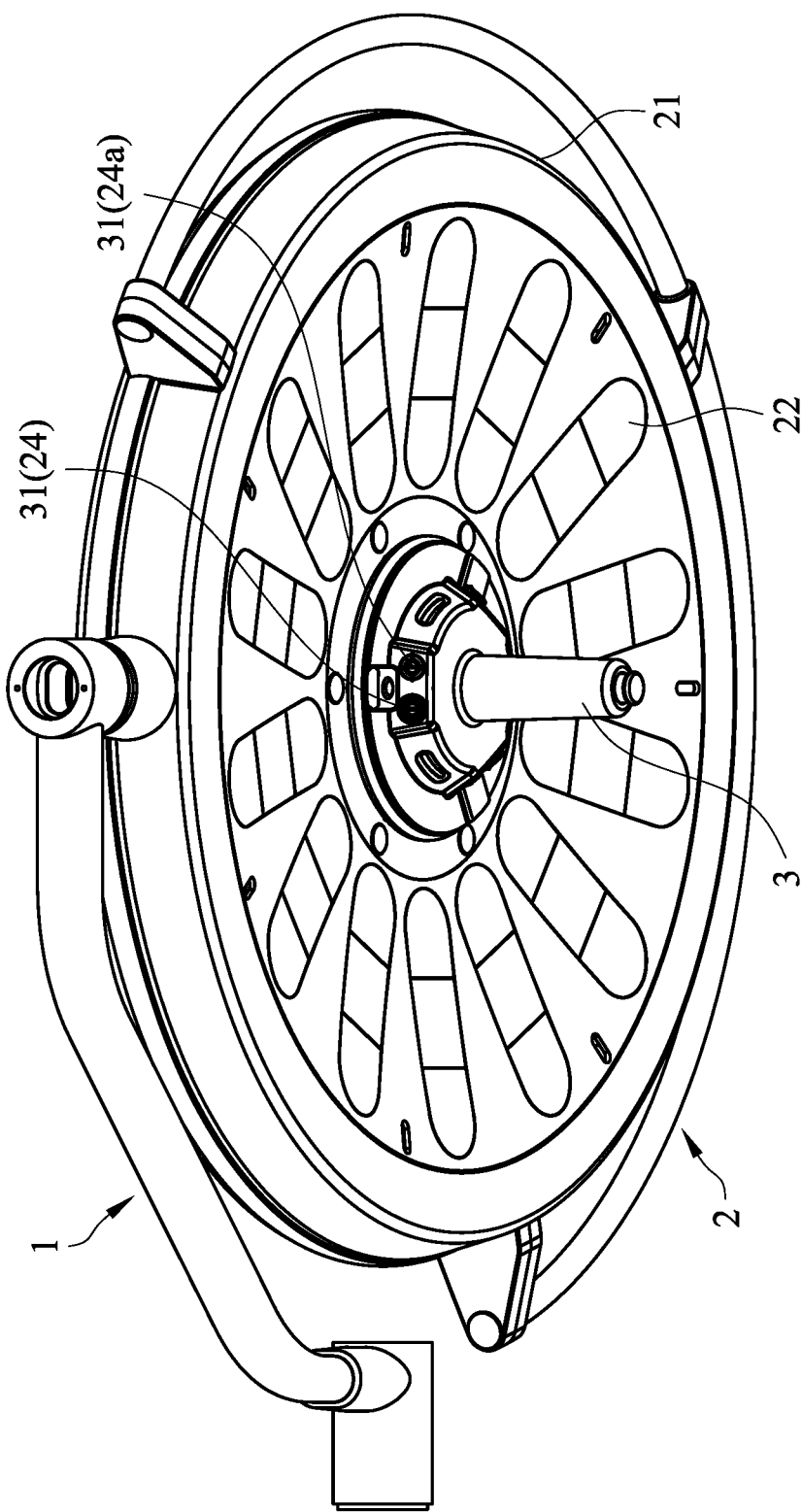
FIG. 2 is a perspective view showing a light head of the arrangement of the present invention.
Figure 3:
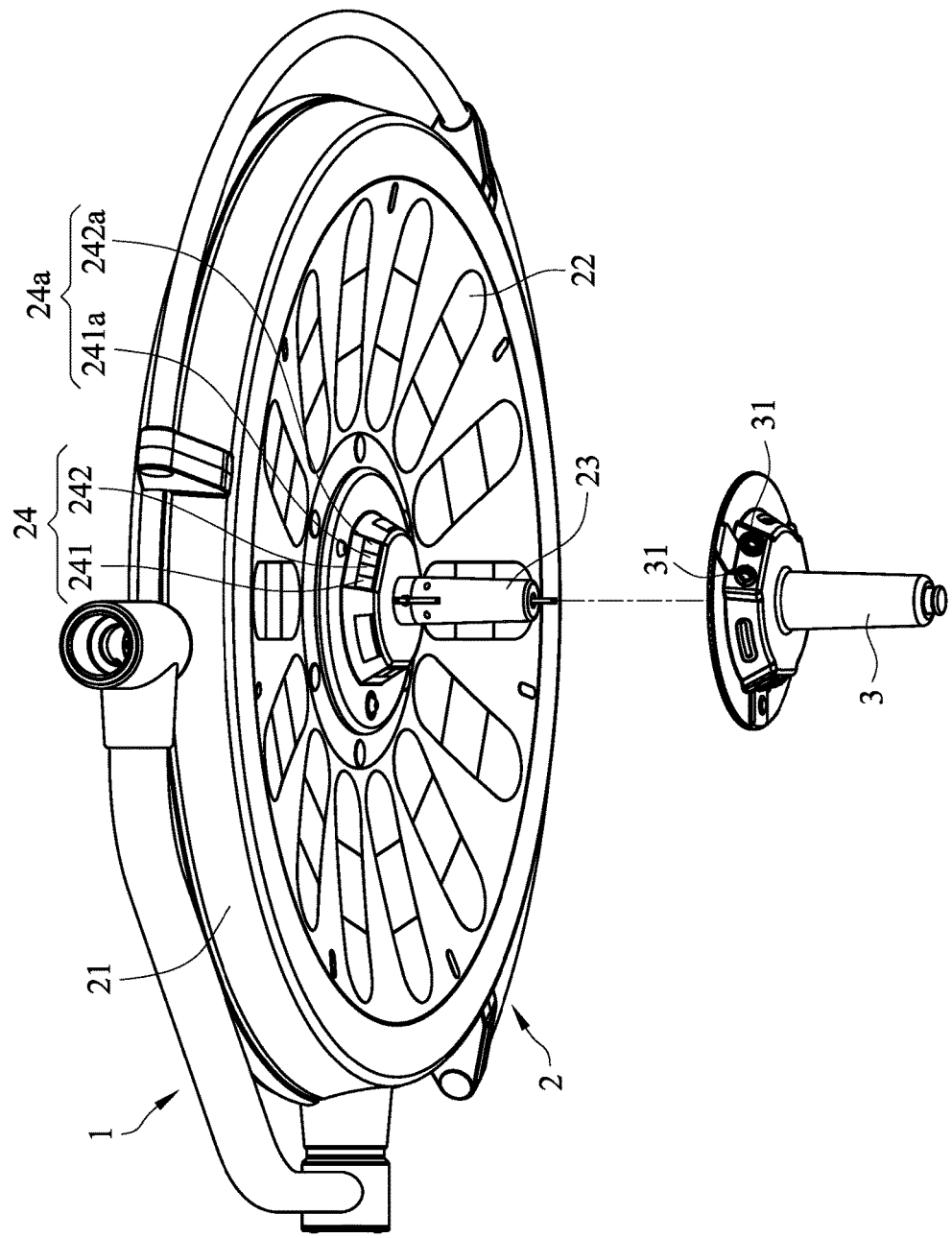
FIG. 3 is an exploded view of the light head of the arrangement of the present invention.
Figure 4:
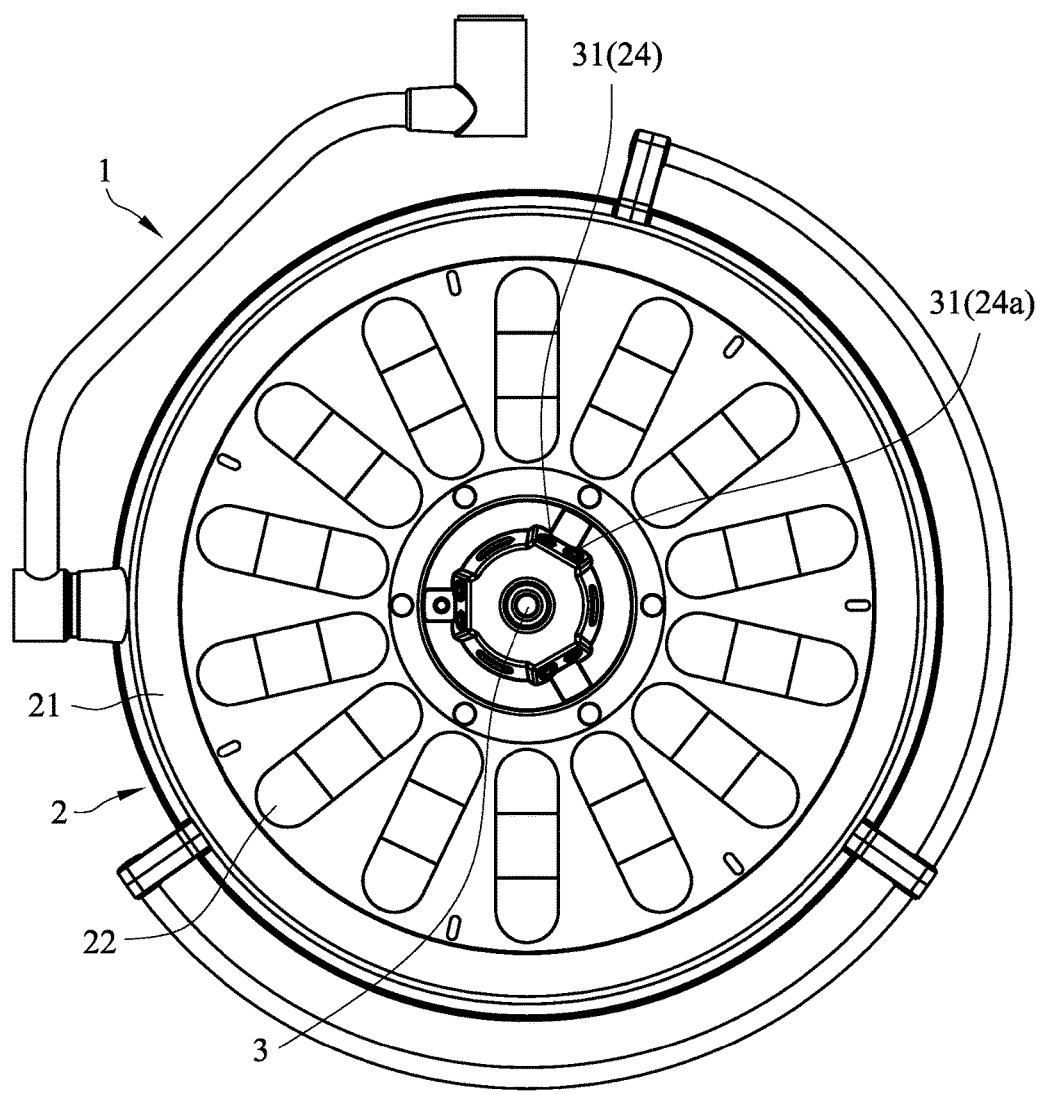
FIG. 4 is a bottom view of the light head of the arrangement of the present invention.

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 5:
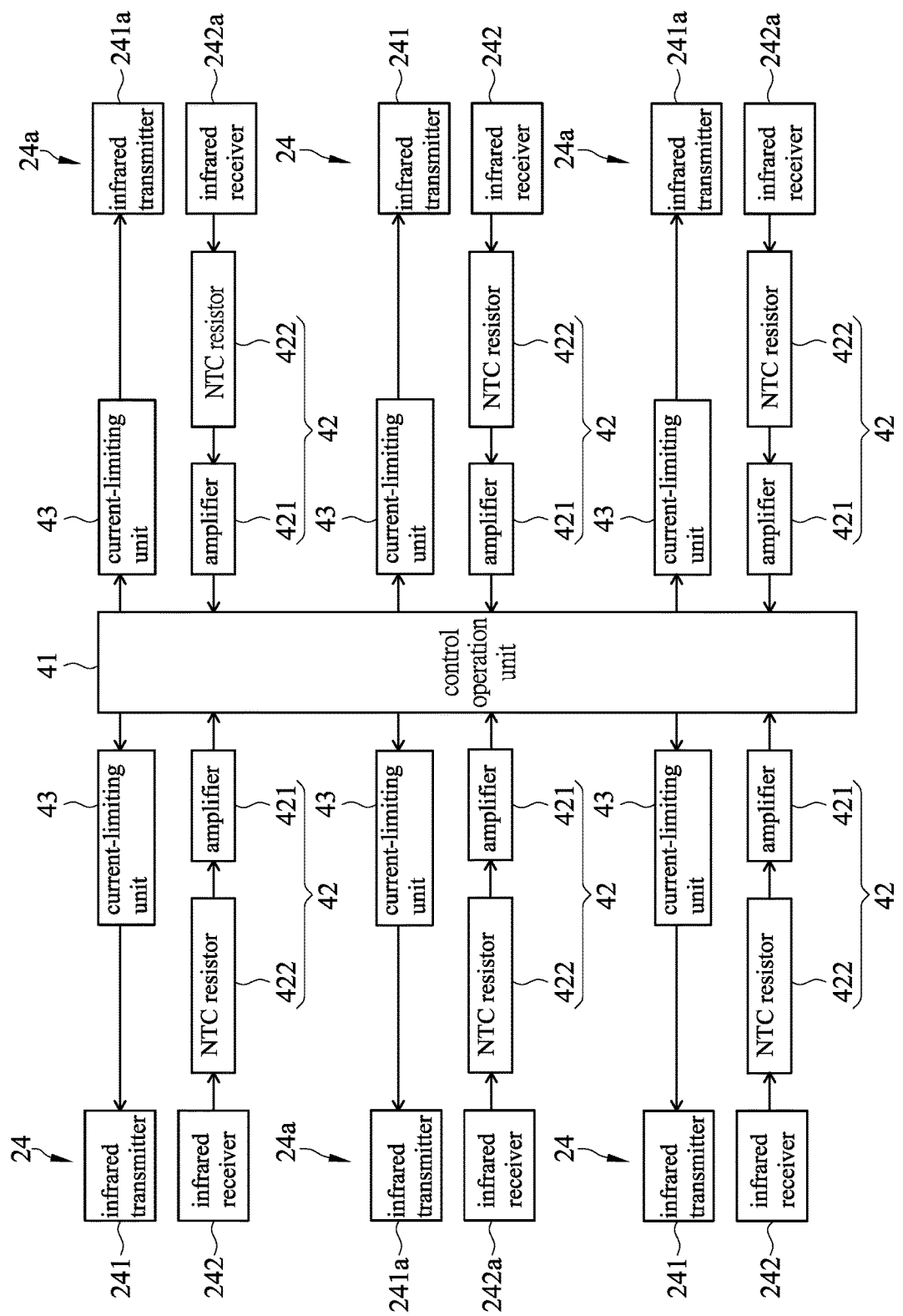
FIG. 5 is a block diagram illustrating a compensation control mechanism of the present invention.

Referring to FIGS. 1-5, which are respectively a schematic view illustrating an entire arrangement of the present invention, a perspective view showing a light head of the arrangement of the present invention, an exploded view of the light head of the arrangement of the present invention, a bottom view of the light head of the arrangement of the present invention, and a block diagram illustrating a compensation control mechanism of the present invention, as shown in the drawings, the present invention provides an illumination control device of surgical light, which comprises, at least:

a suspension or support system 1;

one or multiple light heads 2, which are carried on the suspension or support system 1, each of the light heads 2 comprising a housing 21, one or multiple light sources 22 mounted in the housing 21 for illumination, an unsterilizable grip 23 mounted to the housing 21 for hand holding and moving the light heads 2, and one or multiple detection pairs mounted on the unsterilizable grip 23 for receiving an infrared signal transmitted therefrom and reflected back by an external object in order to conduct control and adjustment of lighting, an arrangement of first and second detection pairs 24, 24a being taken as an example in the instant embodiment of the present invention, wherein each of the light heads 2 comprises one or multiple bidirectional illumination adjustment units and each of the bidirectional illumination adjustment units comprises first and second detection pairs 24, 24a respectively controlling adjustment of the light sources 22, each of the detection pairs 24, 24a comprising an infrared transmitter 241, 241a and an infrared receiver 242, 242a, and also comprises a light source driver (not shown) that operatively couples the light sources 22 and the detection pairs 24, 24a;

a compensation control mechanism 4, which is connected to each of the detection pairs 24, 24a and comprises a control operation unit 41 and a plurality of environment temperature compensation units 42 connected to the control operation unit 41, the compensation control mechanism 4 further comprising a plurality of current-limiting units 43 connected to the control operation unit 41, the current-limiting units 43 being respectively connected to the infrared transmitters 241, 241a, the environment temperature compensation units 42 being respectively connected to the infrared transmitters 241, 241a of the first and second detection pairs 24, 24a, or being alternatively and respectively connected to the infrared receivers 242, 242a of the first and second detection pairs 24, 24a, wherein in an embodiment shown in FIG. 5 of the present invention, an arrangement that the environment temperature compensation units 42 are respectively connected to the infrared receivers 242, 242a of the first and second detection pairs 24, 24a is taken as an example for illustration; and a sterilizable grip 3, which is mounted on the unsterilizable grip 23 and comprises a guide channel 31 formed therein to correspond, in position, to each of the first and second detection pairs 24, 24a so as to allow an infrared signal to pass therethrough, allowing a surgeon to control the illumination while relocating the light heads 2 during surgical procedures, the sterilizable grip 3 being structured for being mounted/dismounted without the use of a tool. As such, a novel surgical lighting illumination control device is formed with the combination of the above technical features.

To operate the present invention, medical personnel firstly mount the sterilizable grip 3 on the unsterilizable grip 23 to have the guide channels 31 of the sterilizable grip 3 respectively corresponding to the first and second detection pairs 24, 24a, so that the medical personnel may hold the unsterilizable grip 23 by means of the sterilizable grip 3 in order to move, with the aid of the suspension or support system 1, the light heads 2 to a desired location. During the movement of the light heads 2, the hands of the medical personnel (such as fingers of the hands) may operate the first and second detection pairs 24, 24a associated with a desired one of the guide channels 31, the guide channels 31 being helpful in precisely isolating and separating a sterile area and a non-sterile area, so that the infrared transmitter 241, 241a is blocked by the hands and a signal is reflected back to the infrared receiver 242, 242a and the light source driver is caused to control the illumination intensity of lighting of the light sources 22, such as activating one of the bidirectional illumination adjustment units of the light head 2 so that the first detection pair 24 sequentially increments, grade by grade, the illumination intensity of the light sources 22 of the light head 2 by a predetermined interval of grades between the maximum and minimum levels; activating one of the bidirectional illumination adjustment units of the light head 2 so that the second detection pair 24a sequentially decrements, grade by grade, the illumination intensity of the light sources 22 of the light head 2 by a predetermined interval of grades between the maximum and minimum levels; simultaneously activating the bidirectional illumination adjustment units of the light head 2 so that the first and second detection pairs 24, 24a turn on or off the light sources 22 of the light head 2; and simultaneously and persistently activating the bidirectional illumination adjustment units of the light head 2 so that the first and second detection pairs 24, 24a, after the lapse of a predetermined period of time, turn on or off the light sources 22 of the remaining light heads 2 of the surgical light.

Further, the first and second detection pairs 24, 24a may be operated in combination with an infrared remote controller (not shown), such that infrared receivers 242, 242a of the first and second detection pairs 24, 24a may receive an illumination control signal emitting from the infrared remote controller to conduct control of the illumination intensity of the light sources 22 from a remote site.

An internal temperature of the surgical light and temperatures of the infrared transmitters 241, 241a increase with time of operation, leading to an increase of resistances of circuits of the infrared transmitter 241, 241a and a reduction of transmission power thereby affecting a distance range of detecting a reflective object and eventually making the operation inaccurate. Thus, in use of the present invention, the compensation control mechanism 4 provides compensation of temperature variation and regulation of operation frequency of each of the detection pairs 24, 24a. During a period of operation, the characteristics of the environment temperature compensation units 42 that the resistance is decreased when the environment temperature increases is applied to stabilize an output of amplification power of compensation circuitry of each of the environment temperature compensation units 42 and to prevent feedback power of each of the infrared receivers 242, 242a from being reduced by the increase of temperature thereby maintaining a stable intensity of a signal fed back to the control operation unit 41.

Further, the infrared transmitter 241, 241a of each of the detection pairs 24, 24a is subjected to calculation conducted by the control operation unit 41 to emit a different frequency during output of a signal and the current-limiting units 43 respectively provide the infrared transmitters 241, 241a with transmission of infrared light of different frequencies. The infrared receivers 242, 242a of the detection pairs 24, 24a, upon receipt of the different frequencies from the infrared transmitters 241, 241a, feed back the signals to the control operation unit 41 for signal processing and decoding.

In the instant embodiment, the unsterilizable grip 23 is provided with six sets of infrared transmitter 241, 241a and infrared receiver 242, 242a. Each of the infrared transmitters 241, 241a and each of the infrared receivers 242, 242a are coded and assigned by the control operation unit 41 with different frequencies for output so that each of the infrared transmitters 241, 241a transmits a different frequency in order to prevent different infrared receivers 242, 242a from supplying incorrect signals to the control operation unit 41, whereby an effect of preventing the infrared transmitters 241, 241a and the infrared receivers 242, 242a from mutual interference in a short distance.

In the instant embodiment, the control operation unit 41 can be an integrated circuit, a microchip, or a logic circuit in order to suit the needs of different applications.

In the instant embodiment, each of the environment temperature compensation units 42 comprises an amplifier 421 connected to the control operation unit 41 and a negative temperature coefficient (NTC) resistor 422 connected between the amplifier 421 and the infrared transmitter 241, 241a. As such, due to the characteristics of the NTC resistor 422 that the resistance thereof decreases with an increase of environment temperature, a stable output of amplification power of compensation circuitry of the amplifier 421 may be achieved and feedback power of each of the infrared receivers 242, 242a is prevented from being reduced by the increase of temperature, wherein a stable intensity of a signal fed back to the control operation unit 41 can be maintained.

In the instant embodiment, each of the current-limiting units 43 comprises a current-limiting resistor in order to suit the needs for various applications.

Thus, the present invention provides at least the following advantages:

(1) When moving the sterilizable grip 3 that is mounted to the light head 2, surgeons or medical personnel may have their hands blocking openings of the guide channel 31 to directly turn on or shut down the light sources 22 or adjust the illumination intensity of the light sources 22 so that there is no need to wait for other persons to help with the operation of the device and adjustment and control of the lighting can be achieved in the most efficient manner.

(2) The sterilizable grip 3, which can be sterilized repeatedly, is mountable to the unsterilizable grip 23 in such a way that the guide channel 31 thereof does not block the passage for transmission and receiving of an infrared signal by the first and second detection pairs 24, 24a so that increase of the cost for consumable material necessary for surgical operations, such as disposable sterile covers for the grip, can be prevented.

(3) The first and second detection pairs 24, 24a may be structured to receive an illumination control signal emitting from an external infrared remote controller so that when surgeons, who are performing a surgical operation, are not able to control the illumination by themselves, medical personnel who are located outside the sterile area may use the infrared remote controller to help control the light sources 22, whereby the costs of installation of wall-mounted control interfaces and wire laying associated therewith can be saved.

(4) The infrared transmitters 241, 241a and the infrared receivers 242, 242a are prevented from mutually interfering with each other in a short distance range.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

We claim:

1. A surgical lighting illumination control device, comprising:
 a suspension or support system;
 one or multiple light heads carried on the suspension or support system, each of the light heads comprising a housing, one or multiple light sources mounted in the housing for illumination, an unsterilizable grip mounted on the housing for hand holding and moving the light heads, and one or multiple detection pairs mounted to the unsterilizable grip for receiving an infrared signal that is transmitted therefrom and reflected by an external object for conducting control and adjustment of the illumination, each of the detection pairs comprising an infrared transmitter and an infrared receiver;
 a compensation control mechanism connected to each of the detection pairs and comprising a control operation unit and a plurality of environment temperature compensation units connected to the control operation unit; and
 a sterilizable grip mountable to the unsterilizable grip and comprising a guide channel formed therein to correspond, in position, to each of the detection pairs to allow the infrared signal to pass therethrough, allowing a surgeon to control the illumination while relocating the light heads during surgical procedures.

2. The surgical lighting illumination control device according to claim 1, wherein the control operation unit comprises one of an integrated circuit, a microchip, and a logic circuit.

3. The surgical lighting illumination control device according to claim 1, wherein each of the environment temperature compensation units comprises an amplifier connected to the control operation unit and a negative temperature coefficient (NTC) resistor connected to the amplifier.

4. The surgical lighting illumination control device according to claim 1, wherein the environment temperature compensation units are respectively connected to the infrared transmitters of the detection pairs.

5. The surgical lighting illumination control device according to claim 1, wherein the environment temperature compensation units are respectively connected to the infrared receivers of the detection pairs.

6. The surgical lighting illumination control device according to claim 1 further comprising a plurality of current-limiting units connected to the control operation unit, the current-limiting units being respectively connected to the infrared transmitters of the detection pairs.

7. The surgical lighting illumination control device according to claim 6, wherein each of the current-limiting units comprises a current-limiting resistor.

8. The surgical lighting illumination control device according to claim 1, wherein each of the light heads comprises one or multiple bidirectional illumination adjustment units, each of the bidirectional illumination adjustment units comprising first and second detection pairs for controlling multiple light functions.

9. The surgical lighting illumination control device according to claim 8, wherein one of the bidirectional illumination adjustment units of each of the light heads is operable in such a way that the first detection pair sequentially increments, grade by grade, illumination intensity of the light sources of the light head by a predetermined interval of grades between maximum and minimum levels; or alternatively, one of the bidirectional illumination adjustment units of each of the light heads is operable in such a way that the second detection pair sequentially decrements, grade by grade, the illumination intensity of the light sources of the light head by a predetermined interval of grades between the maximum and minimum levels.

10. The surgical lighting illumination control device according to claim 9, wherein one of the bidirectional illumination adjustment units of each of the light heads is operable in such a way that the first and second detection pairs are activated simultaneously to turn on or turn off the light sources of the light heads.

11. The surgical lighting illumination control device according to claim 10, wherein one of the bidirectional illumination adjustment units of each of the light heads is actuated persistently so that the first and second detection pairs, after a lapse of a predetermined period of time, turn on or off the light sources of the remaining light heads of the surgical light.

12. The surgical lighting illumination control device according to claim 11, wherein the detection pairs are operable in combination with an infrared remote controller, so that the detection pairs are allowed to receive an illumination control signal emitting from an external infrared remote controller.

13. The surgical lighting illumination control device according to claim 12 further comprising a light source driver operatively coupling the light sources and the detection pairs.

14. The surgical lighting illumination control device according to claim 13, wherein the sterilizable grip is structured for mounting/dismounting without use of a tool.

* * * * *